(12) United States Patent
Chinami et al.

(10) Patent No.: US 9,066,907 B2
(45) Date of Patent: Jun. 30, 2015

(54) METHODS FOR TREATING BURNS-RELATED SYSTEMIC INFLAMMATORY RESPONSE SYNDROME

(71) Applicant: Biofunctional Structure Research Institute, BFSR Co. Ltd., Fukuoka (JP)

(72) Inventors: Masanobu Chinami, Fukuoka (JP); Chaker N. Adra, Boston, MA (US)

(73) Assignee: Biofunctional Structure Research Institute, BFSR Co. Ltd., Fukuoka (JP)

( * ) Notice: Subject to any disclaimer, the term of this patent is extended or adjusted under 35 U.S.C. 154(b) by 0 days.

(21) Appl. No.: 13/927,813

(22) Filed: Jun. 26, 2013

(65) Prior Publication Data

US 2013/0345153 A1 Dec. 26, 2013

(30) Foreign Application Priority Data

Jun. 26, 2012 (JP) .................. 2012-143554

(51) Int. Cl.
*A61K 38/00* (2006.01)
*A61K 39/00* (2006.01)
*C07K 14/00* (2006.01)
*C07K 14/47* (2006.01)
*A61K 38/17* (2006.01)

(52) U.S. Cl.
CPC ............. *A61K 38/17* (2013.01); *A61K 38/1709* (2013.01)

(58) Field of Classification Search
CPC ... A61K 38/00; A61K 39/00; A61K 38/1709; A61K 38/17; A61K 2039/6053; C07K 14/47
See application file for complete search history.

(56) References Cited

FOREIGN PATENT DOCUMENTS

WO WO 2008/073466 6/2008

OTHER PUBLICATIONS

Zhu, W., et al. alphaA-crystallin in the pathogenesis and intervention of experimental murine corneal neovascularization. Experimental Eye Research, 2012, vol. 98, p. 44-51.*
Masilamoni et al., The protective effect of alpha-crystallin against acute inflammation in mice. Biochim Biophys Acta. Jun. 10, 2005;1740(3):411-20. Epub Nov. 17, 2004.

* cited by examiner

*Primary Examiner* — Robert Landsman
*Assistant Examiner* — Bruce D Hissong
(74) *Attorney, Agent, or Firm* — Wolf, Greenfield & Sacks, P.C.

(57) ABSTRACT

A topical preventative medicament against burns-related systemic inflammatory response syndrome containing a low-molecular-weight chaperone as the main active ingredient.

6 Claims, 4 Drawing Sheets

METHODS FOR TREATING BURNS-RELATED SYSTEMIC INFLAMMATORY RESPONSE SYNDROME

RELATED APPLICATIONS

Foreign priority benefits are claimed under 35 U.S.C. §119 (a)-(d) or 35 U.S.C. §365(b) of Japanese application number 2012-143554, filed Jun. 26, 2012.

TECHNICAL FIELD

The present invention relates to a topical preventative medicament against burns-related systemic inflammatory response syndrome.

BACKGROUND OF INVENTION

If someone suffers a burn at their workplace or at home, for example, the conventional advice is to cool the affected area by holding it under running water or similar for the requisite time (e.g. 15 to 30 minutes). If no running water is available nearby, it is desirable to cool the affected area by applying, for example, a poultice containing a cooling agent (e.g. as described in Patent Reference 1). Particularly if the burn is severe, advice and treatment need then to be sought at a medical institution without delay. Treatment appropriate to the depth of the burn can then be provided by the medical institution.

In the case of severe burns, there are times when simply cooling the affected area will not necessarily be sufficient as emergency treatment to be given at the stage before medical advice can be sought at a medical institution.

That is to say, an inflammatory reaction may be elicited by a range of mediators such as inflammatory cytokines produced and released locally or systemically when a victim suffers burns, and this may develop into a condition known as systemic inflammatory response syndrome (SIRS). One cause of SIRS is thought to be the release of cytokines from immunological cells against proteins denatured as a result of the burn.

If the victim goes into SIRS, the symptoms may progress rapidly, leading to septicemia or shock and even death in some cases. In the case of severe burns, it is extremely important to take emergency action to suppress SIRS the same time as applying cooling.

The present invention was devised in the light of these circumstances and provides a topical preventative medicament against burns-related systemic inflammatory response syndrome capable of suppressing burns-related SIRS by being applied directly to the affected area when someone has suffered a burn.

SUMMARY OF THE INVENTION

In order to overcome the current problem described above, the topical preventative medicament against burns-related systemic inflammatory response syndrome in this invention contains a low-molecular-weight chaperone as its main active ingredient. In addition to the low molecular-weight chaperone, the medicament can further contain one or more of (i) a water-soluble fullerene, (ii) histamine and (iii) a buffer.

According to one aspect of the invention, a topical medicament against burns-related systemic inflammatory response syndrome is provided. The medicament contains one or more low-molecular-weight chaperones as the main active ingredient. The chaperone may be any of the molecules or classes of molecules as described in detail below. In important embodiments, the low molecular-weight chaperone is a protein with a homo-oligomeric structure and 9-48 associated subunits with molecular weight of 12-43 kDa. In important embodiments, the low molecular-weight chaperone is a small heat shock protein. In important embodiments, the low molecular-weight chaperone is αB-crystallin.

The topical preventative medicament, in any of the embodiments as described above, can optionally contain a water-soluble agent for enhancing tissue penetration, such as a water soluble fullerene.

The topical preventative medicament, in any of the embodiments as described above, can optionally histamine.

The topical preventative medicament, in any of the embodiments as described above, can optionally contain a buffer.

According to another aspect of the invention, a method of treating a burn is provided. According to another aspect of the invention, a method of increasing the survival chances in an animal having a severe burn is provided. According to another aspect of the invention, a method of inhibiting the development or progression of SIRS is provided. According to another aspect of the invention, a method is provided for suppressing rises in one or more of TNF-α and white blood cell count following severe burns. The methods described in this paragraph involve administering topically to a subject an effective amount of any one of the topical preventative medicaments described above.

According to another aspect of the invention, a pharmaceutical preparation is provided. The pharmaceutical preparation comprises a chaperone for treating a burn. The treatment can be topical treatment. The chaperone can be any one or more of the chaperones described herein. The pharmaceutical can be any of the topical preventative medicaments described herein.

According to another aspect of the invention, a medical treatment system is provide. The system is a bottle or container having a spray nozzle and containing any of the topical preventative medicaments described herein. In any of the forgoing embodiments the chaperone can be present at a concentration of 1-100 µM, 10-80 µM or 25-75 µM. In any of the foregoing embodiments, histamine can be present, and present at a concentration of 0.05-1.0 µM, 0.05-0.5 µM or 0.05-0.1 µM. In any of the foregoing embodiments, the medicament can be an aqueous buffered solution, at 7.5-8.5. In any of the foregoing embodiments, the medicament can contain a buffer present at 10-50 mM or even 20-30 mM. In any of the foregoing embodiments, the buffer can be phosphate buffer.

Taking the invention of claim 1, there can be provided a topical preventative medicament against burns-related systemic inflammatory response syndrome that is capable of treating a burn if applied to the affected area immediately following a burn because it incorporates a low-molecular-weight chaperone as its main active ingredient. In some embodiments, the medicament suppresses burns-related SIRS. In some embodiments, the medicament ameliorates the side effects associated with one or more of a first degree burn, a second burn and a third degree burn. In some embodiments, the medicament enhances healing of a burn by, for example, speeding the process of healing or lessening (relative to an untreated burn) the extent of the damage resulting from the burn.

Moreover, in important embodiments, there is provided a topical preventative medicament, e.g., against burns-related systemic inflammatory response syndrome, with high levels of pharmaceutical stability and safety because the low-molecular-weight chaperone is αB-crystallin, which is ubiquitous in almost all systemic tissues of the body.

DETAILED DESCRIPTION

Figure 1:
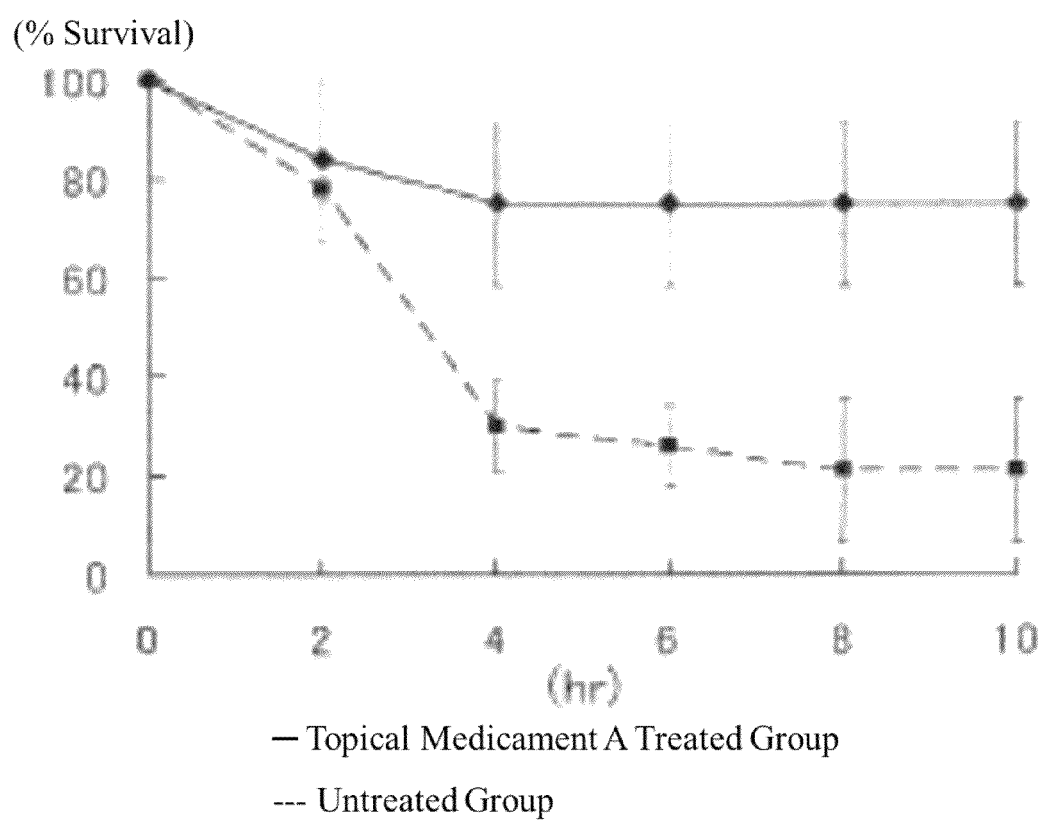
FIG. 1. Is a graph showing the mean survival and standard error at each point for five runs with ten animals (5 sample animals, 5 controls).

The present invention provides a topical preventative medicament against burns-related systemic inflammatory response syndrome, containing a low-molecular-weight chaperone as its main active ingredient.

Burns are injuries sustained by the epidermis or subcutaneous tissue due to heat or chemical substances. In particular, the concept of burns in the context of this specification includes not only heat burns caused by heat from hot water or hot oils, but also chemical burns caused by chemical products such as acids or alkalis, electric shock burns caused by electric current and the like, and radiation burns caused by high-dose radiation.

Burns are classified according to the depth of the injury into first (I), second (II) and third (III) degrees. In first-degree burns, dilatation of the blood vessels causes erythema. In second-degree burns, there is blistering due to vascular hyperpermeability and halting of the blood flow. Third-degree burns involve cutting off of the blood flow and necrosis.

As a rule, second-degree burns can be treated, but wound closure cannot be expected in third-degree burns unless a skin graft is applied. Moreover, severity differs depending not only on the depth but also the breadth of the burn.

The treatment of extensive burns requires fluids to counter shock in the early stages after the injury, infection control until closure of the wound, nutritional management by central venous or tube feeding, and skin grafts and general surgical interventions to save life. However, in severe cases, the victim's life often cannot be saved despite these measures.

As severity cannot be satisfactorily assessed from burn area alone, the burn index (BI: Body Index) represented by the formula below, which takes account of depth and area, is used to assess this.

BI=[area of second-degree burn (%)/2]+area of third-degree burn (%)

Local therapies to treat wounds immediately after a burn occurs include 1) cooling of the heat wound: as a rule, cooling for at least thirty minutes under running water, 2) wound treatment: disinfecting with 0.02-0.5% chlorhexidine and treating with ointments, and 3) special treatment: in full-circumference burns to the extremities of third degree or higher, the blood flow may be obstructed and compartment syndrome develop. If tissue pressure reaches 40 mmHg or more, escharotomy is performed without delay.

Conservative local therapies include 1) closure: azulene ointment, Eksalb, gentamycin sulfate ointment or fradiomycin sulfate dressings are used for shallow burns up to IIs, but for deeper burns of IId or III when there is thick eschar and a bacteria phase readily forms beneath it, silver sulfadiazine creams or mafenide acetate creams are used as these penetrate well even into thick eschar, 2) water treatment (warm bath treatment, shower baths) and 3) bandaging.

Moreover, local surgical treatments include 1) debridement (removal of necrotic tissue) and 2) skin grafts: carried out on third-degree burns when epithelialization cannot be expected. This is usually autologous skin graft. Skin grafts are carried out early on to reduce illness duration and preserve function. Culturing techniques for graft epithelium have also been improving of late and as this is now even covered by health insurance, it is starting to be applied even to extensive burns and is contributing to improved survival rates.

However, as the rescue rate is much lower if BI exceeds 100 (J Jpn Surg Soc 85: 739-748, 1985), treatments that will improve rescue rates are being sought.

Against this general background, the present inventors noticed the cytoprotective effect of low-molecular-weight chaperones against heat treatment. Following intense research to find agents that would fulfill the role of novel treatment for severe burns, they discovered surprisingly that applying a low-molecular-weight chaperone to the affected area—something that had never been tried before—had the effect of greatly improving survival rates from severe burns. They devised the invention of the present application based on these findings.

The present invention relates to a topical preventative medicament to treat burns, and is particularly useful against SIRS in life-threatening severe burns, characterized in that it contains a low-molecular-weight chaperone as its main active ingredient. Molecular chaperones are proteins that assist the non-covalent folding or unfolding of other proteins. One major function of chaperones is to prevent newly synthesized polypeptide chains and assembled subunits from aggregating into nonfunctional structures. It is for this reason that many chaperones, but by no means all, are also heat shock proteins. (HSP initially came from "heat shock", but later on, involved many other factors associated with stresses which induce abnormal conformations; chemical, physical and degenerative like Alzheimer βamyloidosis.)

Molecular chaperones can be divided into two species; large ones which are 60-90 k dalton (kD) of proteins, eg. HSP60/70/90, and small ones or HSPs (sHSP) which are less than about 30 kD, typically 20-30 kD, eg sHSP16.5/20/27, Crystallin $\alpha$A/$\alpha$B. At least 10 sHSP (Hsp:B1,B2, B3, B4, B5, B6, B7, B8, B9 and B10) are found in human and $\alpha$B-crystallin is classified into 5B among them. sHSP is immediately produced in response to various stimuli, under control by heat shock factors, caused by not only high temperature but also under stresses; pH, abnormal pressure, endoplasmic stress (induced by irregular proteins produced in the cellular ribosome). sHSPs trap substrate unfolded/immature substrate proteins (non-native states) by targeting their hydrophobic portions in ATP-independent fashion and transfer them to HSP60/70/90. Thus sHSPs are primary chaperone molecules for cellular metabolic maintenance, replication and apoptosis.

The topical preventative medicament against burns-related systemic inflammatory response syndrome of the present embodiment may obviously be used in humans, but may also be used in animals other than human beings, including mammals.

Proteins belonging to the class of so-called small heat shock proteins (sHSP) are ideal as low-molecular-weight chaperones to be used in this topical medicament.

Low-molecular-weight chaperones include proteins with a homo-oligomeric structure and 9-48 associated subunits with molecular weight of 12-43 kDa and are present ubiquitously in the living world. Such chaperones can be characterized by having an α-crystallin domain comprising about ninety amino acid residues, but they exhibit low sequence homology and the amino acid sequences enclosed by the N-terminal and C-terminal are extremely diverse.

While not wishing to be bound by any theory, with low-molecular-weight chaperones, it is thought that substrate binding sites open up when the homo-oligomer is subjected to stress such as heat, exposing richly lipophilic regions and suppressing the irreversible aggregation of denatured proteins. In other words, low-molecular-weight chaperones have molecular activity that serves to prevent the irreversible aggregation of other proteins, but they do not support ATP-dependent refolding such as seen with Hsp70 or chaperones. Accordingly, it is thought that substrate supplemented by low-molecular-weight chaperone will be released from substrate/low-molecular-weight chaperone complexes by the action of other molecular chaperones such as the Hsp104 and Hsp70/40 systems, and will be refolded.

It thus is believed that this topical medicament will control SIRS quickly without the need for ATP as a result of the low-molecular-weight chaperone suppressing the irreversible aggregation of denatured protein in the affected area, which event otherwise would trigger the immunological reaction leading to SIRS.

Incidentally, it is desirable for the topical medicament to be in the form of an aqueous fluid. If designed like this, there will be little irritation of the affected area and penetration of the low-molecular-weight chaperone into the affected area can take place efficiently. This will also have the effect of keeping the affected area moist and preventing drying.

This topical medicament will be extremely useful as an everyday medicinal product to keep available, for example, in the home or workplace. In other words, by using it without delay on a severe burn before the victim can be seen at a medical center or taken away as an emergency, it will be possible to prevent the onset or worsening of SIRS and improve rescue rates for victims as much as possible.

It is therefore advisable to keep the topical medicament in a refrigerator or similar when not being used with a view to preventing deterioration due to long-term storage. Storage in a refrigerator is also convenient in order to cool the affected area when the product is used.

There are no particular restrictions on the method by which this topical medicament is used, but one approach would be to use it following the cooling of the affected area under running water described earlier. However, in emergency situations when running water is not available, the topical medicament should be used in conjunction with cooling of the affected area. That is to say, the topical medicament may be applied without cooling the affected area under running water. In particular, this type of approach would seem to be important in situations when there would be concern about the progression of SIRS with cooling for long periods.

It is also desirable to add the low-molecular-weight chaperone to an aqueous buffer for the topical medicament, so as to keep the low-molecular-weight chaperone stable in an active state over long periods, such as for 3 months, 6 months, 9 months, twelve months or even years. There are no particular restrictions on the buffer solution to be used as such a medium as long as it can buffer any changes in pH during storage, does not hamper the opening of substrate binding sites of the oligomer in order to activate the low-molecular-weight chaperone as described later, and also has no adverse effects on the body or the affected area (for example, irritation or mutagenicity, etc.).

Examples of such buffers taking well-known materials include phosphate buffer, buffers using HEPES (4-(2-hydroxyethyl)-1-piperazine ethane sulfonic acid) and buffers using MOPS (3-morpholinopropane sulfonic acid).

The concentration of the low-molecular-weight chaperone in the topical medicament is, for example, 1-100 μM, preferably 10-80 μM and more preferably 25-75 μM.

If the concentration of the low-molecular-weight chaperone is less than 1 μM, there will be very little low-molecular-weight chaperone per unit volume and it will be less likely to suppress SIRS. Moreover, concentrations exceeding 100 μM give no marked increase in SIRS control and are undesirable economically. It will be understood, however, that concentrations above 100 μM can be used.

The topical medicament can be both economical and provide satisfactory SIRS control by setting the concentration of the low-molecular-weight chaperone to within the above range.

A tissue penetration enhancer can also be added to the topical medicament. For example, a water-soluble fullerene may also be added to the topical medicament. Such fullerenes typically carry charged groups such as hydroxyl or amine functionalities. The ability of the low-molecular-weight chaperone to penetrate cell membranes can be improved by adding a water-soluble fullerene, and SIRS can be still better suppressed.

The concentration of this added fullerene may be set, for example, at 0.5-2% weight per volume and in some embodiments 1-2%. If the fullerene content is less than 0.5%, very little advantage in terms of aiding cell membrane penetration by the low-molecular-weight chaperone is seen. Using more than 2% does not provide any great improvement in cell membrane penetration by the low-molecular-weight chaperone and is uneconomic. It will be understood, however, that concentrations above 2% can be used. Setting the content of water-soluble fullerene at 0.5-2% and preferably 1-2% is economic and assists penetration of cell membranes by the low-molecular-weight chaperone.

The topical medicament may also incorporate histamine. Histamine is generally believed to aggravate SIRS. However, studies by the inventors indicated that adding histamine to the topical medicament helps to control the onset of SIRS and contributes to improved survival rates by raising the local penetrability of the low-molecular-weight chaperone.

The concentration of histamine added may be set, for example, at 0.05-1.0 μM, preferably at 0.05-0.5 μM and more preferably at 0.05-0.1 μM. If the histamine content goes below 0.05 μM, hardly any SIRS-suppressing effect is seen. Levels above 1.0 μM cannot be expected to provide any marked improvement in SIRS suppression and are not economic. It will be understood, however, that concentrations above 1.0 μM can be used. Setting the content of the water-soluble histamine in the topical medicament at 0.05-1.0 μM, preferably at 0.05-0.5 μM and more preferably at 0.05-0.1 μM is economic and enables the SIRS-suppressing effect to be elicited.

The low-molecular-weight chaperone incorporated into the topical medicament can be αB-crystallin.

Crystallins is the general title given to specific water-soluble proteins in the crystalline lens, and their name is derived from the fact that they are transparent proteins. The crystalline lens of man is made up mainly of the proteins α-, β- and γ-crystallin.

Alpha-crystallin forms large associates through the auto-association of the subunit proteins αA- and αB-crystallin, and is understood to manifest its chaperone function to maintain the transparency of the lens through interaction with β- and γ-crystallin. However, no abnormality in lens function has been demonstrated in mice in which αB-crystallin has been knocked out. Besides the lens, it is present also in the heart, skeletal muscle, kidney, lung, CNS glial cells and so on.

AlphaB-crystallin belongs the heat-shock protein (Hsp) family, and in particular has a high level of homology with the low-molecular-weight Hsp27. It therefore is likely that Hsp27 could be used in combination with or as a substitute for αB-crystallin. In other words, low-molecular-weight chaperones incorporated in this topical medicament also include Hsp27. Put another way, in important embodiments, sHSPs with an α-crystallin domain may be used as the low-molecular-weight chaperone incorporated in the topical medicament.

When αB-crystallin is used as the low-molecular-weight chaperone in the topical medicament, its stability can be increased by setting the pH of the buffer solution mentioned earlier at 7.5-8.5.

However, in order for the αB-crystallin oligomer to break down and be activated, dissociation of the C-terminal IXI motif from the substrate binding site under the low-pH conditions prevalent at sites of inflammation is required, and there is a risk that strong buffer might rather reduce the effect.

The concentration of the buffering ingredient, such as phosphate, HEPES or MOPS should thus be set at a level (buffer capacity) that contributes to the storage stability (stable pH) of the low-molecular-weight chaperone during storage, while ensuring that buffering performance is readily attenuated or lost (pH change) when the medicament is applied to the affected area during use.

For example, if using phosphate buffer as the buffer solution, it should be set at 10-50 mM and preferably 20-30 mM.

With the other buffer solutions too, the concentration of the buffering ingredient appropriate for the topical medicament may be determined as required by checking SIRS suppression in accordance with each of the test methods outlined below. Opening of substrate binding sites of the oligomer occurs at high temperatures, as indicated by the name 'heat shock protein', but it can also take place due to changes in pH as well as phosphorylation by enzymes. With this topical medicament, the change in pH at the time of use acts as the trigger to promote activation, and consequently, even though the low-molecular-weight chaperone is in a stable state during storage, it can be rapidly changed to active mode when it is used.

The topical medicament is described in more detail below through specific examples.

EXAMPLES

Preparation of a topical preventative medicament against burns-related systemic inflammatory response syndrome The preparation of this topical medicament is described first. In the present embodiment, reference is made to a topical preventative medicament against burns-related systemic inflammatory response syndrome containing αB-crystallin as the low-molecular-weight chaperone, but it goes without saying that other low-molecular-weight chaperones could be used.

There are no particular restrictions on the processes whereby the αB-crystallin, which is the essence of the present topical medicament, is produced. Recombinant αB-crystallin expressed in *E. coli* was used here. This was prepared as follows.

Firstly, *E. coli* BL-21 transformed with an His-tagged PET vector encoding αB-crystallin was incubated overnight in LB medium at 37° C.

Next, isopropyl-β-D-thiogalatoside (IPTG) was added to the medium to a final concentration of 1 mM and it was further incubated for four hours at 37° C. so as to induce overexpression of the protein.

The cells were collected by centrifugation (8000×g, 20 mins, 4° C.) and the supernatant fluid removed. They were then suspended in pH 7.8 lysis buffer comprising 0.25 g/mL lysozyme, plus 25 mM Tris/50 mM NaCl/0.9% glucose/1 mM EDTA containing a protease inhibitor cocktail (Sigma) and were solubilized in ice with ultrasound.

The solubilized fraction was separated by centrifugation (10,000×g, 20 mins, 4° C.) and the resulting supernatant fluid was dialyzed with 20 mM phosphate buffer, pH 7.8, containing 0.5 M table salt and applied to a Ni-chelating column (Pharmacia) equilibrated with the same buffer.

After the column had been flushed with 20 mM imidazole equilibrated buffer, the fraction was eluted with 20 mM imidazole equilibrated buffer.

The eluted fraction was then concentrated with Amicon and dialyzed with 20 mM phosphate buffer. The resulting fluid was taken as the topical preventative medicament against burns-related systemic inflammatory response syndrome (hereafter, topical medicament A) and subjected to the tests described below.

In order to apply the topical preventative medicament against burns-related systemic inflammatory response syndrome to affected areas in the explanations below, it was decided that 1 mL of a product at a concentration of 50 μM calculated from the molar extinction coefficient should be sprayed on having removed LPS (lipopolysaccharides) with ET Clean (JNC K.K.).

Confirmation of Mortality Rate Reduction—Test 1

Next, mice that had suffered burns were used in tests to confirm reductions in mortality rate depending on whether or not a topical preventative medicament of this embodiment against burns-related systemic inflammatory response syndrome had been applied.

The tests were carried out with reference to a method established as a model reflecting life-threatening severe burns. This was considered to provide an ideal evaluation system for tests to confirm reductions in mortality rates using a topical preventative medicament of this embodiment against burns-related systemic inflammatory response syndrome.

Specifically, the fur was shaved from an area 3 cm in diameter on the backs of ICRSW male mice and depilation was carried out with Veet (Reckitt Benckiser Japan).

Next, 20 mg/kg of pentobarbital was given by the intraperitoneal route, and 25% of the animals' total body surface area (TBSA) with the depilated area in the center was immersed in hot water at 100° C. for eight seconds. The animals were monitored and mortality rates compared after six hours in the group treated with topical medicament A (N=5) and the untreated group (N=5). The results are shown in FIG. 1.

It is evident from FIG. 1 that whereas survival in the untreated group was about 20% over the first ten hours (21.0±14.3%), it was about 75% (75.0±16.6%) in the group treated with topical medicament A. Tests for significant difference between the two groups also suggested that the survival rate was significantly higher (p=0.0047) as a result of applying topical medicament A (applying 50 μM αB-crystallin).

These observations confirmed that applying a low-molecular-weight chaperone provides benefits in terms of reducing mortality rates following serious burns.

Confirmation of Mortality Rate Reduction—Test 2

Next, mice that had received burns in the same way as in the preceding tests were used in tests to confirm mortality rate reductions depending on the use or otherwise of a topical preventative medicament of this embodiment against burns-related systemic inflammatory response syndrome, but to which a water-soluble fullerene had been added.

Specifically, a medicament was prepared combining 1% of water-soluble C60 fullerene (Vitamin C60 Co., Tokyo) with the topical medicament A prepared in Test 1 for confirming mortality rate reductions (topical medicament B).

Tests were then carried out by the method used in Test 1 for confirming mortality rate reductions. Three groups were established for the tests, namely, treated with topical medicament B, treated with topical medicament A, and untreated. These were compared ten hours after receiving the burns. The results of these tests are set out in FIG. 2.

Figure 2:
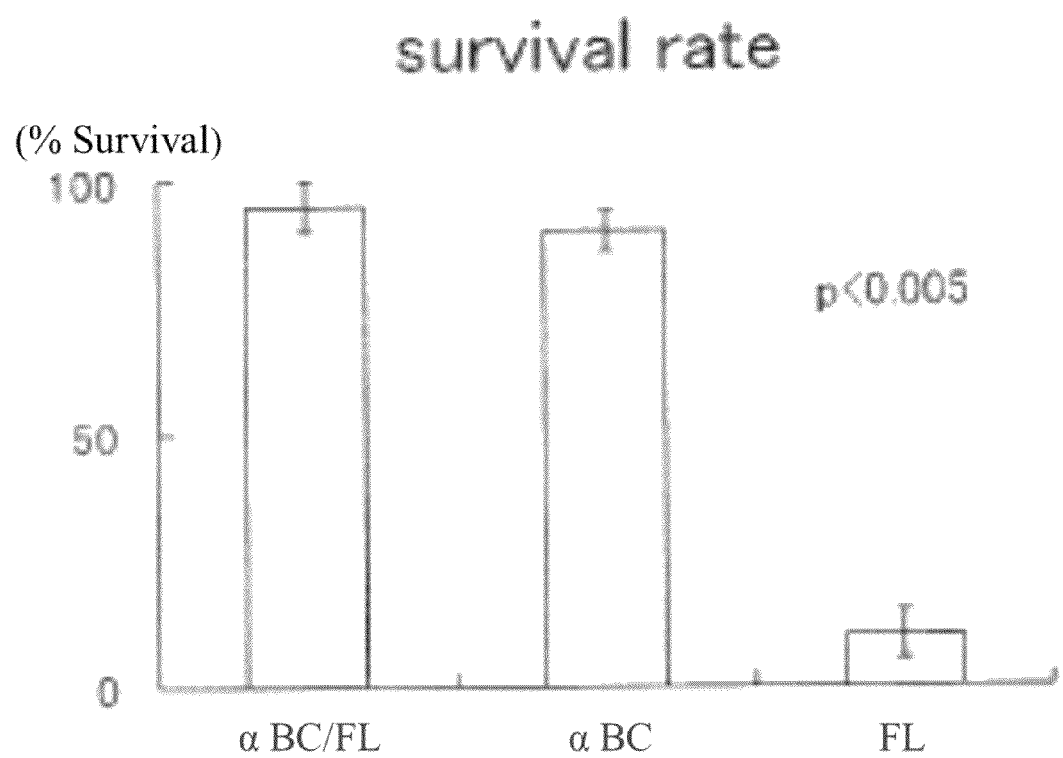
FIG. 2 Is a graph showing that survival was about 100% in the group treated with topical medicament B that had been mixed with a water-soluble C60 fullerene to improve cell membrane penetrability ($p<0.005$), and the level was higher than in the group treated with topical medicament A.

As is clear from FIG. 2, survival was about 100% in the group treated with topical medicament B that had been mixed with a water-soluble C60 fullerene to improve cell membrane penetrability (p<0.005), and the level was higher than in the group treated with topical medicament A.

This confirmed that the mortality rate reduction seen with a low-molecular-weight chaperone can be further improved by combining the use of a water-soluble C60 fullerene.

Confirmation of Mortality Rate Reduction—Test 3

Next, mice that had received burns in the same way as in the two preceding tests were used in tests to confirm mortality rate reductions depending on the use or otherwise of a topical preventative medicament of this embodiment against burns-related systemic inflammatory response syndrome, but to which histamine had been added.

Specifically, a medicament was prepared adding histamine to a final concentration of 1 μM to topical medicament A prepared in Test 1 for confirming mortality rate reductions (topical medicament C). As the control, a medicament was prepared adding anti-histamine to a final concentration of 1 μM to topical medicament A (topical medicament D).

Tests were then carried out by the method used in Test 1 for confirming mortality rate reductions. Two groups treated with topical medicament C and with topical medicament D were established for the tests and they were compared ten hours after receiving the burns.

Consequently, whereas no marked reduction in mortality rate was seen in the group treated with topical medicament D compared to that treated with topical medicament A described earlier, the group treated with topical medicament C showed a marked reduction in mortality rate compared to those treated with topical medicament D or topical medicament A. It seemed that the life-prolonging action had been increased by histamine, which promotes vascular endothelial permeability, and that it had conversely been decreased by adding an anti-histamine.

These findings served to confirm that the effect of topical medicament A to reduce mortality rates could be improved still further by combining the use of histamine.

Tests to Confirm Suppression of Rises in TNF-α and White Blood Cell Count

Rises in TNF-α and white blood cell count are generally seen in SIRS following shock due to burns. Validation was carried out to confirm that these topical medicaments act to suppress rises in TNF-α and white blood cell count following severe burns.

Two groups were established for these tests, one treated with topical medicament A (N=5) and another untreated group (N=5). TNF-α (pg/mL) and white blood cell count (cells/μL) were determined three hours after the burns had been received. An ELISA kit (Shibayagi, Japan) was used to determine mouse TNF-α. The results are shown in FIG. 3 and FIG. 4.

Figure 3:
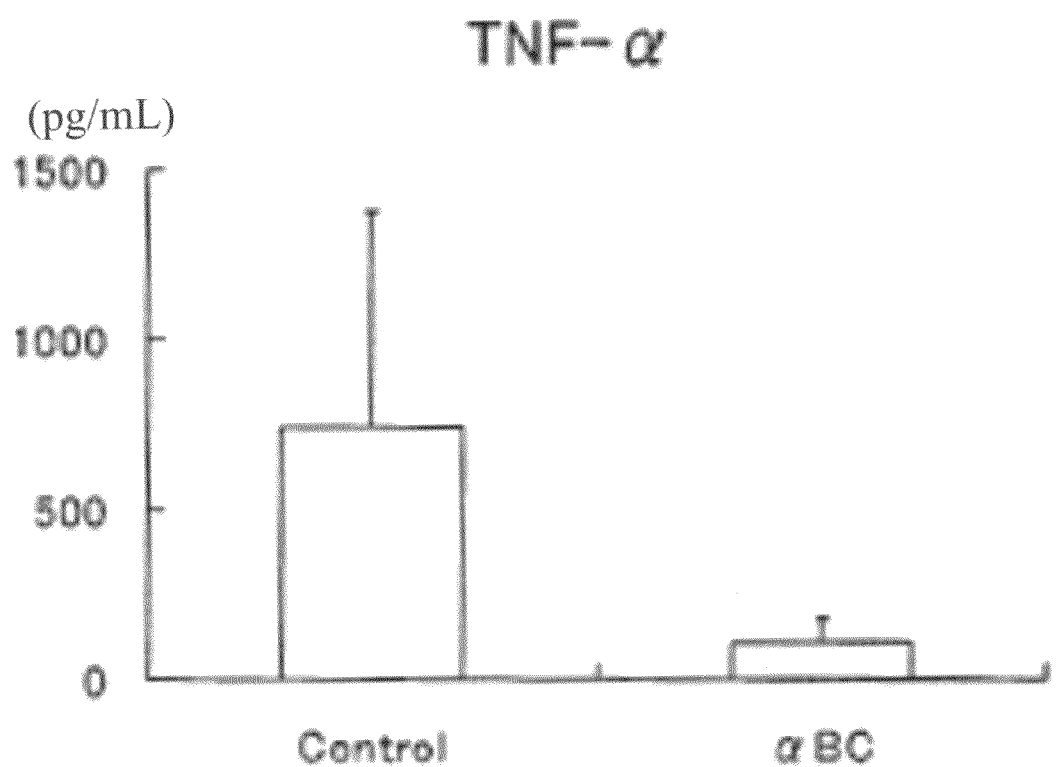
FIG. 3 Is a graph showing test results demonstrating that the level of serum TNF-$\alpha$ was markedly suppressed by the application of topical medicament A compared to no treatment.

As is clear from FIG. 3, the results of these tests demonstrated that the level of serum TNF-α was markedly suppressed by the application of topical medicament A compared to no treatment.

Figure 4:
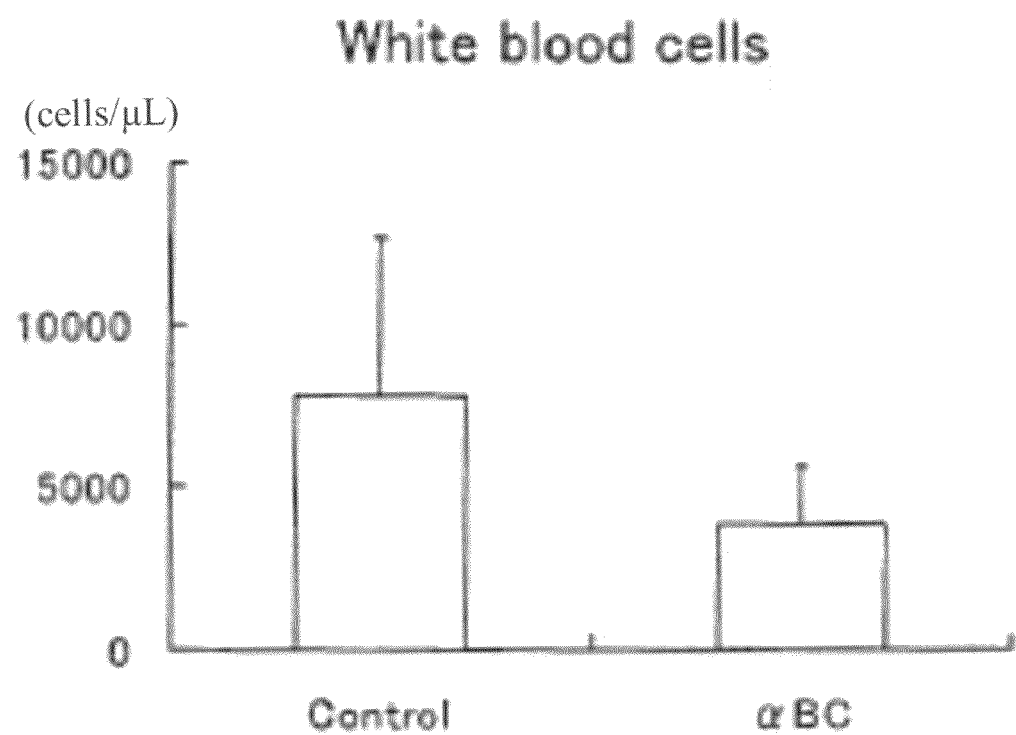
FIG. 4 Is a graph showing that the white blood cell count was markedly controlled by the application of topical medicament A compared to no treatment.

As is clear also from FIG. 4, the white blood cell count was markedly controlled by the application of topical medicament A compared to no treatment.

It was evident from these findings that this topical medicament is highly effective for suppressing the marked rises in TNF-α and white blood cell count seen after burns, and it was suggested that this could suppress burns-related SIRS and contribute to reduced mortality rates.

As stated above, because the topical preventative medicament of the present invention against burns-related systemic inflammatory response syndrome contains a low-molecular-weight chaperone as its main active ingredient, it is possible to provide a topical preventative medicament against burns-related systemic inflammatory response syndrome capable of suppressing SIRS due to burns by applying it immediately to the affected area when someone suffers a burn.

Finally, the descriptions of each of the above embodiments are examples of the present invention and the invention is not limited to the embodiments described above. Therefore various changes can be made as appropriate to the design and the like to produce embodiments other than each of those described above, as long as they do not deviate from the technical concept of the invention.

What is claimed is:

1. A method for treating burns-related systemic inflammatory response syndrome, comprising administering topically to a subject in need of treatment to the site of a burn an effective amount of a crystallin chaperone.

2. The method of claim 1, wherein the chaperone is alpha B-crystallin.

3. The method of claims 1 or 2, wherein the crystallin chaperone is in an aqueous solution.

4. The method of claim 3, wherein the chaperone is present at a concentration of 1-100 μM.

5. The method of claim 3, wherein the chaperone is present at a concentration of 10-80 μM.

6. The method of claim 3, wherein the chaperone is present at a concentration of 25-75 μM.

* * * * *